(12) United States Patent
Palmer et al.

(10) Patent No.: US 7,078,236 B2
(45) Date of Patent: *Jul. 18, 2006

(54) METHODS OF INDUCING OVULATION

(75) Inventors: Stephen Palmer, Plympton, MA (US); Sean McKenna, Duxbury, MA (US); Mark Tepper, Canton, MA (US); Aliza Eshkol, La Rippe (CH); Michael C. MacNamee, Cambridgeshire (GB)

(73) Assignee: Applied Research Systems ARS Holding N.V., Curacao (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/169,183

(22) Filed: Jun. 28, 2005

(65) Prior Publication Data

US 2006/0003925 A1    Jan. 5, 2006

Related U.S. Application Data

(60) Division of application No. 10/014,812, filed on Dec. 14, 2001, now Pat. No. 6,953,774, which is a continuation-in-part of application No. 09/928,268, filed on Aug. 10, 2001, now abandoned.

(60) Provisional application No. 60/224,962, filed on Aug. 11, 2000.

(51) Int. Cl.
*A61K 38/24* (2006.01)
*C12N 15/15* (2006.01)

(52) U.S. Cl. .................... 436/65; 435/69.2; 530/313; 530/388.24; 514/2

(58) Field of Classification Search ............. 435/69.2; 514/2, 253.13; 544/372, 141; 436/65; 530/313, 530/388.24
See application file for complete search history.

(56) References Cited

U.S. PATENT DOCUMENTS 6,423,710 B1 *  7/2002  Martins et al. .......... 514/231.5

OTHER PUBLICATIONS

Tsafriri et al. (1996) Oocyte maturation involves compartmentalization and opposing changes of cAMP levels in follicular somatic and germ cells: studies using selective phosphodiesterase inhibitors. Dev. Biol. vol. 178, pp. 393-402.*
Taylor et al. (1997) Src tyrosine kinase activity in rat thecal-interstitial cells and mouse TM3 Leydig cells is positively associated with cAMP-specific phosphodiesterase activity. Mol. Cell. Endocrinol. vol. 126, pp. 91-100.*
Ovulation Calendar (2005) "luteal phase" //www.oulation-calendar.com/hlp-d04-luteal-phase.html, p. 1.*

* cited by examiner

*Primary Examiner*—Jon Weber
*Assistant Examiner*—Samuel Wei Liu
(74) *Attorney, Agent, or Firm*—Howrey LLP; David W. Clough

(57) ABSTRACT

The present invention relates to methods of inducing ovulation in a female host comprising the administration of a non-polypeptide cyclic adenosine monophosphate (cAMP) level modulator to the female host. In another aspect, the invention provides for specific administration of the phosphodiesterase inhibitor prior to the luteal phase of the host's ovulatory cycle. Preferred non-polypeptide cAMP level modulators include phosphodiesterase inhibitors, particularly inhibitors of phosphodiesterase 4 isoforms.

17 Claims, 10 Drawing Sheets

METHODS OF INDUCING OVULATION

CROSS-REFERENCE TO RELATED APPLICATIONS

The present application is a divisional of U.S. application Ser. No. 10/014,812, filed Dec. 14, 2001, now is U.S. Pat. No. 6,953,774, which is a continuation-in-part of U.S. application Ser. No. 09/928,268 filed Aug. 10, 2001, now abandoned, which claims the benefit of U.S. Provisional Application No. 60/224,962, filed Aug. 11, 2000, each of which is incorporated herein in its entirety.

FIELD OF THE INVENTION

The present invention relates to methods of enhancing fertility in a female host by inducing ovulation with the administration of a non-polypeptide modulator of cAMP levels.

BACKGROUND OF THE INVENTION

Ovulation is the process where an ovum or ova are released from the ovaries. The timing of ovulation within the menstrual cycle is of foremost importance for fertilization. It is well recognized that follicles acquire the ability to ovulate following growth and maturation stimulated by the pituitary gonadotropins. Follicle stimulating hormone (FSH) is predominantly responsible for follicular growth and luteinizing hormone (LH) stimulates ovulation. This coordinated process of gonadotropin-stimulated maturation of the follicle ensures delivery of a competent ova at ovulation. The adequately prepared ovum is then available for fertilization by sperm within hours after ovulation.

Ovulation is a finely timed process that is driven by pituitary gonadotropin stimulation of the ovary, and modified by the growth and biochemical (e.g., steroidogenic, inhibin secretion, etc.) response of follicles to the gonadotropin stimulation. During the normal menstrual cycle in women these hormones exhibit cyclic patterns. The menstrual cycle can be functionally divided into three phases: the follicular, the ovulatory and luteal phases. The follicular period begins at the end of the luteal phase of the preceding non-conceptive cycle, prior to or coincident with the onset of menses. The cycle starts with a transient rise in blood levels of FSH that stimulates development of a cohort of ovarian follicles. The size of the follicles recruited to grow is about 5 mm in diameter. In a natural menstrual cycle, usually one large or dominant follicle is established during the follicular phase, and it is committed to growth to maturation. In humans, the size of the follicle that is considered ready to ovulate is about 15 mm or more in diameter.

The second critical event that occurs in the ovary during the follicular phase is that granulosa cells within the ovarian follicles acquire receptors for LH and become increasingly responsive to LH. Secretion of estradiol and estrone from the ovary increases slowly at first, in parallel to the increasing diameter of the follicle and sensitivity of the follicle to LH. The relatively rising levels of estrogen and inhibin cause inhibition of gonadotropin releasing hormone (GnRH) secretion from the hypothalamus and gonadotropin secretion from the pituitary. Estrogen production reaches a maximum on the day before the LH peak and the neuroendocrine response to increased estrogen and gradually increasing concentrations of progesterone is the preovulatory release of gonadotropins which is discussed below.

During the ovulatory phase there is a change in the neuroendocrine response to estrogen and progesterone. At this point in the cycle, elevated estrogen elicits a preovulatory surge in serum FSH and LH levels, due to a positive feedback on the hypothalamus, estrogen now stimulating a surge in the levels of GnRH and subsequently FSH and LH release from the pituitary. This surge of gonadotropins induces the completion of follicular maturation and causes rupture of the dominant or Graafian follicle and discharge of the ovum some 16 to 24 hours after the LH peak. During the period following the preovulatory surge, serum estradiol levels temporarily decline and plasma progesterone levels begin to rise.

Following ovulation, the post-ovulatory ovarian follicle cells under the influence of LH are luteinized to form a corpus luteum—the luteal phase. The diagnostic markers of the luteal phase of the menstrual cycle are the marked increase in progesterone secretion by the corpus luteum, and the uterine transformation that occurs in response to progesterone. Associated with luteal progesterone production, there is a less pronounced increase in serum estrogen levels. As progesterone and estrogens increase, LH and FSH decline throughout most of the luteal phase. Towards the end of the luteal phase, in a non-conceptive menstrual cycle, the corpus luteum regresses and serum FSH levels begin to rise to initiate follicular growth for the next cycle.

FSH and LH are distinguished from each other by their ability to stimulate follicular development or ovulation, respectively. Both agents are known to stimulate an increase in intracellular cAMP concentrations. Agents that mimic cAMP such as forskolin or stable analogs of cAMP have been shown, in vitro, to resemble the effects of FSH in granulosa cells from immature follicles, and to resemble the effects of LH in cells from mature follicles. Although alternative intracellular pathways have been proposed for both FSH and LH, it is well accepted that cAMP is stimulated in response to both gonadotropins. If and when elevations in cAMP levels are associated with follicular development and maturation or ovulation induction depends on the cell types and the presence or absence of the respective receptors. Indeed, it has been demonstrated that mice which are deficient in a particular phosphodiesterase have impaired ovulation and diminished sensitivity of granulosa cells to gonadotropins.

Infertility treatments currently in clinical use incorporate some of the regulatory events described above. One agent which stimulates follicular growth and is used for treatment of anovulation is clomiphene. Clomiphene is a nonsteroidal antiestrogen that competes for estrogens at their binding sites. It is thought that clomiphene binds to estrogen receptors in the hypothalamus and pituitary and blocks the negative feedback exerted by ovarian estrogens. The result is increased output of gonadotropins (FSH and LH) during the early part of the follicular phase. The effect of clomiphene is to increase endogenous FSH serum levels and to improve the growth and maturation of follicles. Subsequently either endogenous LH or exogenous LH/CG induce ovulation in these patients.

In addition to clomiphene, women have been treated with ovulation induction regimens which include commercial preparations of the human gonadotropins, including follicle stimulating hormone (FSH) and luteinizing hormone (LH) or chorionic gonadotropin (CG), all of which were first obtained by purification of urine from pregnant women and more recently by recombinant technology. In general, this treatment is highly effective in stimulating folliculogenesis and steroidogenesis. Complications of this treatment result from the fact that these preparations and regimens can over-stimulate follicular development and maturation of follicles. In a subset of patients, the ovary can become hyperstimulated, which may result in multiple ovulations and, consequently, multiple births. Not only can ovarian hyperstimulation be life threatening to the mother, it also typically results in newborns with lower birth weight, who subsequently require intensive care. It is believed that the principal complications attributed to gonadotropin-induced hyperstimulation and multiple pregnancies probably result from the prolonged effects of hCG. In addition, use of gonadotropins in ovulation induction regimens can result in injection site reactions, both local and systemic. Consequently, the development of ovulation induction regimens using orally active agents with milder gonadotropin-like activity as opposed to therapies that use potent injectables would be of substantial benefit. More importantly, it would be a significant advantage if ovulation induction regimens could be developed which result in less ovarian hyperstimulation and, consequently, present less danger to the mother and produce healthier newborns.

SUMMARY OF THE INVENTION

In a first aspect, the invention provides a use of a non-peptide CAMP level modulator, preferably a PDE inhibitor, more preferably a PDE4 inhibitor, for the manufacture of a medicament for the induction of ovulation in a patient.

In a second aspect, the invention provides a use of a non-peptide CAMP level modulator, preferably a PDE inhibitor, more preferably a PDE4 inhibitor, for the induction of ovulation in a patient.

In a third aspect, the invention provides a use of a non-peptide CAMP level modulator, preferably a PDE inhibitor, more preferably a PDE4 inhibitor, for the manufacture of a medicament for the induction of ovulation in a patient, in a regimen whereby follicular maturation is induced with clomiphene or an aromatase inhibitor, preferably an aromatase inhibitor selected from YM-511, Letrozole, Fadrozole, and Anastrozole, more preferably selected from Letrozole and Anastrozole, prior to ovulation induction.

In a fourth aspect, the invention provides a use of a non-peptide CAMP level modulator, preferably a PDE inhibitor, more preferably a PDE4 inhibitor, for the induction of ovulation in a patient, in a regimen whereby follicular maturation is induced with clomiphene or an aromatase inhibitor, preferably an aromatase inhibitor selected from YM-511, Letrozole, Fadrozole, and Anastrozole, more preferably selected from Letrozole and Anastrozole, prior to ovulation induction.

In a fifth aspect, the invention provides a kit for use in inducing ovulation, the kit comprising an ovulation inducing dose of a non-peptide CAMP level modulator, preferably a PDE inhibitor, more preferably a PDE4 inhibitor, and instructions for its use in inducing ovulation.

In a sixth aspect, the invention provides a kit for use in ovulation induction and/or assisted reproductive technologies (ART), the kit comprising sufficient daily doses of FSH and/or a compound having FSH effect, preferably clomiphene or an aromatase inhibitor, more preferably an aromatase inhibitor selected from YM-511, Letrozole, Fadrozole, and Anastrozole, to cause follicular maturation, and an ovulation inducing dose of a non-peptide CAMP level modulator, preferably a PDE inhibitor, more preferably a PDE4 inhibitor, and instructions for the use of the kit in ovulation induction or ART.

In a seventh aspect, the invention provides a use of a non-peptide cAMP level modulator, preferably a PDE inhibitor, more preferably a PDE4 inhibitor, for inducing ovulation in a patient, in a regimen wherein human chorionic gonadotropin (hCG) or LH are also administered to induce ovulation, and the hCG or LH are administered at a reduced dose compared to the amount of hCG or LH normally required to induce ovulation in the same patient.

DETAILED DESCRIPTION OF THE INVENTION

Figure 1:
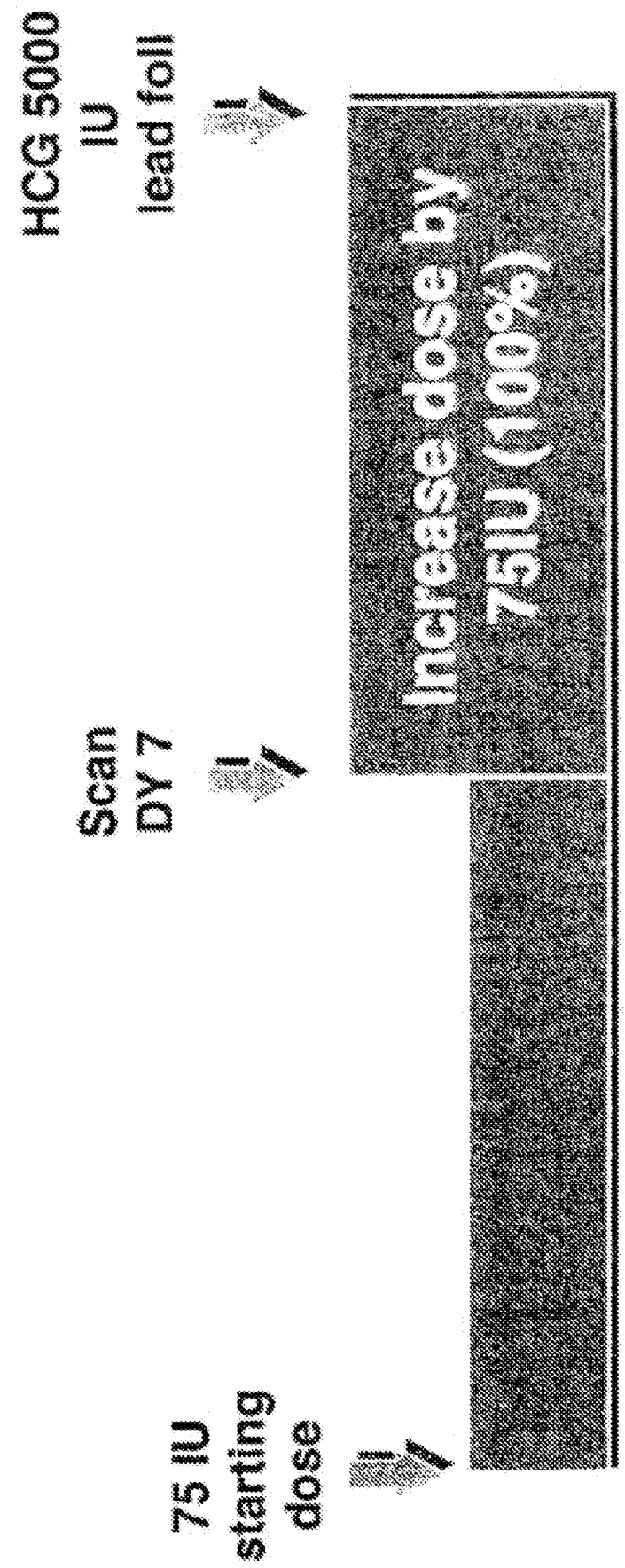
FIG. 1 is a schematic representation of a generalized ovulation induction regimen in humans.

The present invention relates to methods of improving fertility in a female host comprising the administration of a non-polypeptide cyclic adenosine monophosphate (CAMP) level modulator to the female host. In another aspect, the invention provides for specific administration of the non-polypeptide CAMP level modulator to induce ovulation of the dominant mature follicle prior to the luteal phase of an ovulatory cycle. Preferred non-polypeptide CAMP level modulators include phosphodiesterase inhibitors, particularly inhibitors of phosphodiesterase 4 isoforms.

Although effects of PDE inhibitors on LH-stimulated steroidogenesis from granulosa cells, in vitro, have been reported, the present invention describes two novel findings. First, the PDE inhibitors fail to enhance FSH-stimulated follicular growth in viva, despite the accepted role of CAMP in both FSH and LH cellular pathways. Moreover, evidence is presented that PDE inhibitors did enhance gonadotropin-stimulated steroidogenesis in vitro, which further exemplifies the novel activity of the PDE inhibitor on LH-dependent ovulation. Second, the PDE inhibitors increased the ovulation rate, in vivo, in the absence of added LH or hCG. Considering the oral activity of PDE inhibitors, this second finding provides the basis for the first potential injection-free regimen for ovulation induction, since the PDE inhibitors can be used in conjunction with existing regimens as described below.

The invention also provides for the stimulation of follicular development prior to the administration of a non-polypeptide CAMP level modulator which comprises the administration of an agent which increases FSH concentrations during the follicular phase of the host's ovulatory cycle. The objective of the invention in increasing FSH relates solely to follicular development and maturation and not ovulation induction. Preferred agents include FSH, itself, clomiphene, selective estrogen receptor modulators, aromatase inhibitors and selective modulators of the neuroendocrine regulation of FSH production.

In still another aspect, the invention provides for the co-administration of a non-polypeptide CAMP level modulator with LH or chorionic gonadotropin (CG) prior to the luteal phase of the female host's ovulatory cycle. Co-administration can occur sequentially or simultaneously, as well as by the same or different modes of delivery (e.g., parenterally and or orally). In addition, the invention provides for the use of lower concentrations of LH or CG administered to the host than concentrations that are used in current ovulation induction regimens and thereby lowering the likelihood of ovarian hyperstimulation.

Additionally, the present invention provides for the use of a non-polypeptide CAMP level modulator as a therapeutic agent in replacement of or to enhance the effect of hCG or LH in the collection of oocytes for in vitro fertilization.

Thus, the invention provides for the use of a non-polypeptide CAMP level modulator as a small molecule therapeutic (e.g., phosphodiesterase inhibitors) that is administered orally rather than by injection, the required route of administration for proteins and the mode of administration in current ovulation induction regimens. Oral administration avoids the acute and systemic side effects associated with such injections. Foremost, the small molecule therapeutic is effective in inducing ovulations and can be administered alone or with or without LH or CG and alternatively, in lower concentrations of LH or CG than are currently used, and thus, lessen the occurrence of ovarian hyperstimulation and its associated risks. Consequently, multiple births and life threatening complications for the mother and newborns can be averted. In addition, the present invention provides for the opportunity of earlier diagnostic testing for pregnancy than current ovulation induction regimens involving the use of CG.

The treatment methods of the invention will be useful for treatment of infertility in humans, but also in other mammals (such as horses and livestock, e.g., cattle, sheep, cows and the like) and other species, such as piscine (i.e., fish) and avian (i.e., fowl).

I. Definitions

In general, the following words or phrases have the indicated definition when used in the description, examples and claims.

"Administration" refers to the delivery of a therapeutic agent into a female host. In the context of the present invention, this would include the delivery of a non-polypeptide cAMP level modulator and/or an agent which increases FSH concentrations. This term is more fully described under the section entitled, "Pharmaceutical Compositions" contained herein.

"Ovulation" for the purposes herein refers to the process where an ovum or ova are released from the ovaries. As midcycle approaches, there is a dramatic rise in estrogen, followed by an LH and to a lesser extent an FSH surge. This triggers the dominant follicle to ovulate. Ovulation consists of rapid follicular enlargement followed by protrusion of the follicle from the surface of the ovarian cortex. Ultimately, rupture of the follicle results in the extrusion of an oocyte-cumulus complex. The remnant of the dominant follicle then reorganizes to become the corpus luteum.

"Anovulation" refers to a lack of ovulation.

"Non-Polypeptide CAMP Level Modulator" refers to compounds that are not composed of amino acids in their entirety, irrespective of glycosylation, and act, directly or indirectly, to increase intracellular levels of CAMP. Such compounds can increase CAMP levels by stimulating CAMP synthesis or by inhibiting its degradation, or both. Examples of modulators which increase the synthesis of cAMP include activators of adenyl cyclase such as forskolin. Examples of modulators that decrease CAMP degradation include inhibitors of phosphodiesterases such theophylline.

"Female Host" means an individual of female gender of a species to which agents are administered in accordance with the present invention. Humans other mammalians and other species such as fish and fowl are included by definition herein.

"Phosphodiesterase Inhibitor" refers to chemical compounds which block or inhibit phosphodiesterases (PDE's) whose action is to inactivate their cyclic nucleotide targets (i.e., CAMP and cGMP) by hydrolytic cleavage of the 3'-phosphodiester bond, resulting in passive accumulation of specific cyclic nucleotides. Inhibitors can be non-selective for all phosphodiesterase isoforms or selective for specific isoforms. See compounds cited herein.

"Phosphodiesterase Isoforms" refers to a family of isozymes or isoforms responsible for the metabolism or degradation of the intracellular second messengers, CAMP and cGMP. Specific isoforms can have highly selective cellular and subcellular localizations. Examples of phosphodiesterase isoforms include PDE3 and PDE4.

"Follicular Phase" refers to the first part of the menstrual cycle and is characterized by a progressive increase in circulating levels of estradiol and inhibin B by the developing Graafian follicle.

"Prior to the Luteal Phase" refers to the period of the menstrual cycle before the shift from the estrogen dominated follicular phase to the progesterone dominated luteal phase. Prior to the luteal phase, the estrogen levels are generally greater than or equal to 150 pg/ml/follicle for a follicle of 16 mm in diameter and the follicle size is generally no less than 14 mm in diameter. These criteria are not absolute and will vary from patient to patient. In the context of the present invention and in terms of the timing of administration of the non-polypeptide CAMP level modulator, the non-polypeptide CAMP level modulator can be administered to a female host at the time point of an existing ovulation induction regimen at which hCG or LH is normally administered to said host.

"Ovulatory Cycle" or "Menstrual Cycle" refer to a series of cyclical events over a species-specific period of time including follicular growth and development, recruitment, selection, dominance, ovulation, and corpus luteum formation and demise. Functionally, the cycle can be divided into three phases, the follicular, the ovulatory and the luteal phases. This cycle can also be referred to the menstrual cycle.

"Ovulation Induction" refers to the process wherein a polypeptide(s) and/or synthetic chemical is used to bring about ovulation in female hosts who are otherwise anovulatory, resulting in induction of follicular rupture and ovulation of fertilizable oocytes. Ovulation induction does not include the preceding events in time during the ovulatory cycle of follicular maturation and development.

"Ovarian Hyperstimulation" refers to pharmacological intervention of an ovulatory or anovulatory menstrual cycle. It entails maturation of multiple follicles resulting in codominance of numerous follicles and the availability of multiple fertilizable oocytes.

"Follicle" refers to the fluid filled sac that surrounds the ovum, the sac also containing granulosa cells.

"Follicular Development" refers to the progressive growth and development of ovarian follicles, particularly during the follicular phase of the ovulatory cycle and leading to the recruitment and dominance of a follicle destined to ovulate.

"Follicle Stimulating Hormone (FSH) and Isoforms" refers to a hormone released by the pituitary that stimulates the growth of ovarian follicles and isoforms of FSH as described, for example, in U.S. Pat. No. 5,087,615, incorporated by reference herein.

"Selective Estrogen Receptor Modulators" refers to chemical compounds or polypeptides that act as an estrogen receptor antagonist at the level of the hypothalamus and the pituitary gland, and as an agonist at the level of the uterus. Examples of such modulators can include tamoxifen, raloxifene, toremifene, clomiphene and droloxifene. Reference Shughrue et al (1999) is hereby incorporated by reference.

"Aromatase Inhibitors" refer to chemical compounds or polypeptides that block or inhibit the activity of aromatase which is an enzyme that converts androgens to estrogens. Examples of aromatase inhibitors include Letrozole, Anastrozole and Vorozole. References Turner et al (2000) and Shetty et al (1997) are hereby incorporated by reference.

"Related Steroidogenic Enzymes" refers to any enzyme that is involved with the catalysis of biochemical reactions leading to the synthesis of estrogen and progesterone including 3-β-hydroxysteroid dehydrogenase and inhibitors of this enzyme include daidzein, genistein, biochanin A and formononetin. Reference Cooke (1996) is hereby incorporated by reference.

"Clomiphene" refers to 2-[4-(2-chloro-1,2-diphenylethenyl)phenoxy]-N,N-diethylethanamine and its salts.

"Lutenizing Hormone" refers to a hormone released by the pituitary that serves the dual purpose of causing a dominant follicle to release its egg and stimulating the corpus luteum to secrete progesterone.

"Reduced concentrations" refers to lower concentrations of an administered agent when compared to standard levels of administered agents. In the context of the present invention, lower concentrations of LH or CG are administered than are administered in existing ovulation induction regimens.

"Existing Ovulation Induction Regimens" refers to current methods of inducing ovulation including the use of clomiphene, gonadotropins (i.e., FSH, LH and CG) or a combination of these agents to promote folliculogenesis and induced ovulation in anovulatory females. The regimens are varied in terms of the timing, frequency and concentration of the agents administered. This definition includes modifications of current regimens which still require the administration of hCG or LH at some time point during the ovulation induction regimen. The following treatises on female infertility, stimulated folliculogenesis and ovulation induction are incorporated by reference herein: Adashi et al (1996) and Shoham et al (1999).

"Chorionic Gonadotropin" refers to a glycoprotein hormone that is biologically and immunologically similar to pituitary LH. In normal pregnancy, CG is produced by the placenta and can be used as a diagnostic marker of pregnancy by elevated levels in serum concentration. The acronym hCG refers to human chorionic gonadotropin.

"Agent which Increases FSH Concentrations" refers to any composition of matter, protein or synthetic chemical, which when administered to a female host increases the serum level concentrations of FSH, either directly or indirectly, by administering FSH itself, or an agent which stimulates its endogenous production or inhibits its endogenous degradation. The definition of this phrase and agent includes compounds which may not increase FSH concentrations but have follicle stimulating hormone biological function and activity.

II. Principles of Ovulation Induction

Problems of inadequate or inappropriate gonadotropin levels have been recognized as causes of ovulatory dysfunction since the 1960s. The clinical effectiveness of the various gonadotropin preparations used was proportional to the amount of FSH administered. Initial evidence suggested that exogenous LH is not required for adequate folliculogenesis during ovulation induction. It became apparent, however, that women given only exogenous FSH fail to produce adequate follicular estradiol for ovulation induction. The presence of at least some amount of exogenous or endogenous LH for ovulation induction in the human appears to be important. FIG. 1 illustrates a schematic representation of a generalized ovulation induction regimen. An FSH preparation is given at 75 IU/day for the first 7 days. At the end of 7 days, an ultrasound scan is taken to assess follicular diameter and serum estradiol is measured. If the follicle is less than 12 mm, the dose of FSH is doubled, and a subsequent scan is taken in another 5–7 days. Patients with follicles ≧15 mm diameter receive an ovulatory bolus dose of hCG.

III. Generalized Ovulation Induction Regimen

Ovulation induction is as much an art as a science. Despite a remarkable array of treatment protocols, no single approach or specific method is uniquely correct. Certain principles do apply, however, and provide the basis for safe and effective treatment. However, it should be noted that the criteria set forth below for inducing ovulation is given for example purposes only and may vary significantly by clinic, patient and the goal of the treatment.

The first cycle usually involves the administration of FSH daily beginning on day 4 to 7 of a withdrawal bleed. Follicle growth and response are monitored by both estrogen levels and ultrasound. Adequate follicle stimulation is usually achieved by 7 to 14 days of continuous FSH administration. Treatment with FSH for less than 8 days is associated with increased spontaneous abortion rates among pregnant patients.

Once sufficient follicle development has been achieved (two 16- to 18-mm follicles together with a progressive rise in serum estrogen to 500 to 1,000 pg/mL), hCG (5,000 or 10,000 IU) is administered. The timing of hCG administration is important because the principal complications attributed to gonadotropin-induced hyperstimulation and multiple pregnancies probably result from the prolonged effects of hCG. Although the half-life of hCG is approximately 8 hours, it may be detectable in the patient's blood for 7 to 10 days after injection and misdiagnosed as a successful treatment pregnancy. Following administration of hCG, the couple is instructed to have intercourse on that night and once or twice more over the next 48 hours.

The fundamental rule regarding gonadotropin administration is that each and every treatment cycle must be individualized, monitored, and adjusted appropriately. Monitoring is necessary not only to enhance ovulation and pregnancy rates but also to reduce the risk of severe ovarian hyperstimulation and its potential consequences and multiple pregnancies.

This is achieved by frequent determinations of plasma/serum estradiol levels and by inspection of the ovaries by ultrasound. Estradiol levels generally correlate with the number of growing follicles but not necessarily with the number of mature follicles. Reliance on estradiol levels as the marker for follicle maturity may erroneously suggest follicle maturity in the presence of multiple small follicles, resulting in premature hCG administration. Because follicular growth correlates directly with ovum maturation, ultrasound assessment of mean follicular diameter may be a better indicator in assessing maturity and timing of hCG administration. Estrogen levels should therefore be used to assess early follicular development as an indicator of gonadotropin response, and ultrasound should be used to assess the number and size of maturing follicles.

The goal of most treatments is to maximize the potential for a singleton pregnancy while reducing the risk of hyperstimulation syndrome. Estradiol levels between 1000 and 1500 pg/mL appear to be optimal, but actual levels may vary depending on the laboratory used and the physician's experience. The risk of hyperstimulation increases with higher estradiol levels. In general, when serum estradiol exceeds 2000 pg/mL, hCG should be administered with great caution or withheld to allow follicles to regress. In hypogonadotropic hypogonadism, the risk of severe hyperstimulation for values greater than 2400 pg/mL is 5% in pregnancy cycles and 1% in non-pregnant cycles. Furthermore, because hyperstimulation tend to correlate with the number of follicles present, a decision to withhold hCG may be also based on an ultrasound finding of 10 or more developing follicles.

The following treatises on female infertility, stimulated folliculogenesis and ovulation induction are incorporated by reference herein: Reproductive Endocrinology, Surgery, and Technology, Volumes 1 and 2; Editors: E. Y. Adashi et al (1996) and Shoham et al (1999).

IV. Methods of the Present Invention

The present invention relates to a method of ovulation induction that comprises the administration of a non-polypeptide cAMP level modulator in an ovulation induction regimen in which the modulator is administered to enhance or substitute the administration of hCG (or LH), which is typically administered prior to the luteal phase of an induced or naturally occurring ovulatory cycle. The modulator can be administered alone or co-administered, either simultaneously or sequentially, with hCG (or LH), as well as by different modes of delivery (e.g., parenterally or orally).

In another aspect, the invention provides for the co-administration, either simultaneously or sequentially, of a non-polypeptide cAMP level modulator with LH or CG prior to the luteal phase of the female host's ovulatory cycle. In addition, since it is believed that the principal complications attributed to gonadotropin induced ovarian hyperstimulation and consequent multiple pregnancies probably result from the prolonged effects of hCG, the invention provides for the use of lower concentrations of LH or CG administered to the host than concentrations that are used in existing ovulation induction regimens and thereby lowering the likelihood of ovarian hyperstimulation, and consequently averting the adverse effects associated with that condition: multiple births, low weight newborns and health complications for the mother.

It should be noted that the administration of non-polypeptide cAMP level modulators have no therapeutic effect on follicular maturation and development during the ovulatory cycle.

Thus, the present invention relates to methods of inducing ovulation in a female host comprising the administration of a non-polypeptide cyclic adenosine monophosphate (CAMP) level modulator to the female host. The non-polypeptide CAMP level modulators act, directly or indirectly, to increase intracellular levels of CAMP. Such compounds can increase CAMP levels by stimulating CAMP synthesis or by inhibiting its degradation, or both. Examples of modulators which increase the synthesis of CAMP include activators of adenyl cyclase such as forskolin. Examples of modulators that decrease cAMP degradation include inhibitors of phosphodiesterases such theophylline. Preferred non-polypeptide CAMP level modulators include phosphodiesterase inhibitors, particularly inhibitors of phosphodiesterase 4 isoforms.

In still another aspect, the invention provides for specific administration of the non-polypeptide CAMP level modulator prior to the luteal phase of the host's ovulatory cycle. As an enhancer or substitute of hCG in an ovulation induction regimen, in which hCG is typically administered towards the end of the follicular phase but prior to the luteal phase of the ovulatory cycle.

The preferred timing of administration of the non-polypeptide CAMP level modulator is prior to the luteal phase of the host's ovulatory cycle.

The invention also provides for the stimulation of follicular development prior to the administration of a non-polypeptide CAMP level modulator for inducing ovulation which comprises the administration of an agent which increases follicular stimulating hormone (FSH) concentrations during the follicular phase of the host's ovulatory cycle. Preferred agents include FSH, itself, clomiphene, selective estrogen receptor modulators, aromatase inhibitors and agents which are not FSH but have FSH biological function and activity. Thus, administration of the agents described herein in a prescribed timing relative to the growth and maturation of the follicle are claimed to improve the process of ovulation and subsequent fertilization that must take place if conception is to occur.

It should be noted that when a non-polypeptide cAMP level modulator is administered alone and not co-administered with hCG, the present invention provides for the opportunity of earlier diagnostic testing for pregnancy than current ovulation induction regimens involving the use of CG.

V. Phosphodiesterase Inhibitors

For phosphodiesterase inhibitors used as non-polypeptide cAMP modulators, essentially any non-toxic inhibitor of PDE can be used in the methods of the invention, including selective and non-selective inhibitors of PDE4. Suitable non-selective inhibitors of PDE4 and combined PDE3/PDE4 inhibitors include theophylline, isobutylmethylxanthine, AH-21-132, Org-30029 (Organon), Org-20241 (Organon), Org-9731 (Organon), Zardaverine, vinpocetine, EHNA (MEP-1), Milrinone, Siguazodan, Zaprinast, SK+F 96231; Tolafentrine (Byk Gulden), Filaminast (Wyeth-Ayerst Pharmaceuticals).

Particularly preferred are selective inhibitors specific for PDE4. Many known selective PDE4 inhibitors fall into one of six chemical structural classes, rolipram-like, xanthines, nitraquazones, benzofurans, naphthalenes and quinolines. Examples of rolipram-like analogs include imidazolidinones and pyrrolizidinone mimetics of rolipram and Ro 20-1724, as well as benzamide derivatives of rolipram such as RP 73401 (Rhone-Poulenc Rorer). Xanthine analogs include Denbufylline (SmithKline Beecham) and Arofylline (Almirall); Nitraquazone analogs include CP-77,059 (Pfizer) and a series of pyrid[2,3d]pyridazin-5-ones (Syntex); Benzofuran analogs include EP-685479 (Bayer); Napthalene analogs include T-440 (Tanabe Seiyaku); and Quinoline analogs include SDZ-ISQ-844 (Novartis).

More preferred are the following:

Compounds disclosed in WO 97/42174 (Pfizer, Inc.):

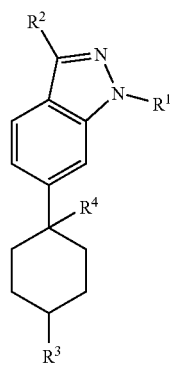

wherein $R^1$ is cyclopentyl or cyclohexy, $R^2$ is ethyl, $R^3$ i-s a carboxylic acid, ester or primary amide, hydroxymethyl or a carbonyl group, and $R^4$ is cyano;

Compounds disclosed in U.S. Pat. Nos. 5,710,160 and 5,710,170 (Merck Frost Canada, Inc.):

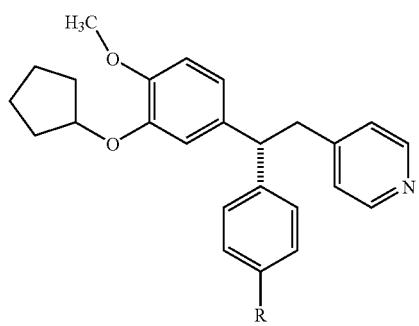

wherein R is selected from H, CO-(4-mepiperazinyl), CO-(pyrrolidinyl), CHNOH, 5-tetrazolyl, (CH)OHCH$_3$, COCH$_3$, CONHSO$_2$CH$_3$, CONHSO$_2$Ph, CONHSO$_2$CF$_3$, CONHSO$_2$C$_6$H$_4$CH$_3$ (o), CH$_2$CONHSO$_2$Ph, CH$_2$CONHSO$_2$CF$_3$, COH(CF$_3$)$_2$ and SO$_2$NHCOC$_6$H$_4$CH$_3$ (o).

Compounds disclosed in WO 98/20007 (Darwin Discovery), represented by:

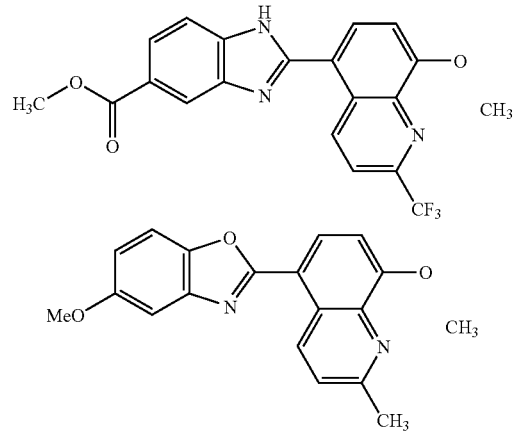

Compounds disclosed in WO 98/14432 (Janssen Pharm NV):

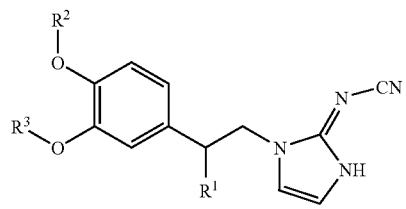

wherein $R^1$ is H or CH$_3$, $R^2$ is CH$_3$ or CHF$_2$, $R^3$ is cyclopentyl, indanyl, cyclopropylmethyl, Ph(CH$_2$)$_5$, THF.

Compounds disclosed in WO 98/18796 (Novartis):

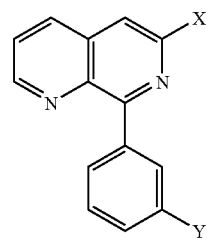

wherein X is NH$_2$, OH, NHPh, NPh$_2$, Ph, C$_6$H$_4$CO$_2$H and Y is Cl, CN, NO$_2$.

Compounds disclosed in WO 97/49702 (Pfizer, Inc.), represented by:

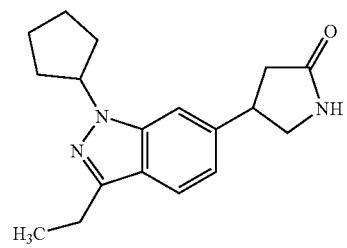

Compounds disclosed in WO 97/48697 (Rhône-Poulenc Rorer):

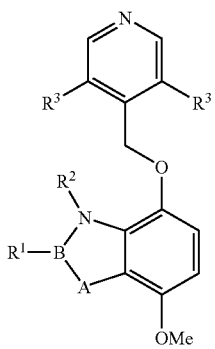

wherein $R^1$ is cyclopentyl, cyclopropyl, $Ph(CH_2)_3$, Benzyl or H, $R^2$ is $CH_3$, Benzyl, Tosyl or H, $R^3$ is $CH_3$ or Cl, A is CH, C-alkyl, O or N, and B is C or N.

Compounds disclosed in WO 98/02440 (Bayer AG):

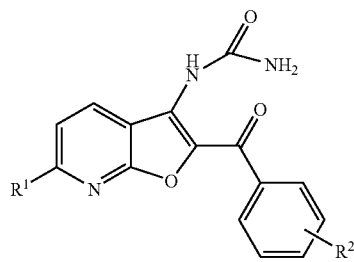

wherein $R^1$ is $CH_3$, OH, Oallyl, $OCH_3$, $C_2H_5$, Propyl or Acetyl, $R^2$ is 3-Cl, 2,4-$Cl_2$, 3-$NO_2$, 3-Br, 4-F, 4-Cl, 2,4-$(CH_3)_2$ or 2,4 $(CH_3O)_2$.

Compounds disclosed in WO 97/44337, WO 97/44036, WO 97/44322 (Chiroscience Ltd.):

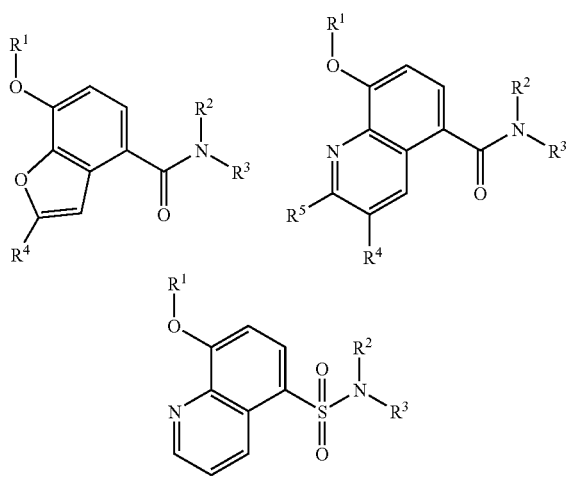

wherein $R^1$ is $CH_3$, Ethyl or Propyl, $R^2$ and $R^3$ are independently selected from H, optionally substituted aryl or heteroaryl, and $R^4$ and $R^5$ are independently selected from acyl, alkyl (optionally substituted with OH, or halogen), aryl, heteroaryl, and acyl substituted with aryl or heteroaryl.

Compounds disclosed in U.S. Pat. No. 6,303,789 (Byk Gulden Lomberg Chemische Fabrik GmbH):

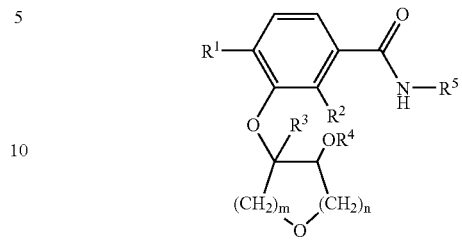

wherein $R^1$ is 1–6C-alkoxy, 3–7C-cycloalkoxy, 3–7C-cycloalkylmethoxy, benzyloxy or 1–4C-alkoxy which is completely or predominantly substituted by fluorine; $R^2$ is hydrogen; and $R^3$ is hydrogen; or $R^2$ and $R^3$ are together a methylene group; $R^4$ is hydrogen, 1–8C-alkyl, 1–6C-alkoxy-1–4C-alkyl, 1–6C-alkylthio-1–4-alkyl, 1–6C-alkylsulfinyl-1–4C-alkyl, 1–6C-alkylsulfonyl-1–4C-alkyl, 1–8C-alkylcarbonyl, 3–7C-cycloalkyl, 3–7C-cycloalkymethyl, phenyl-1–4C-alkyl or 1–4C-alkyl which is completely or predominantly substituted by fluorine; $R^5$ is phenyl, pyridyl, phenyl substituted by $R^{51}$, $R^{52}$ and $R^{53}$ or pyridyl substituted by $R^{54}$, $R^{55}$, $R^{56}$ and $R^{57}$, wherein $R^{51}$ is hydroxyl, halogen, cyano, carboxyl, trifluoromethyl, 1–4C-alkyl, 1–4C-alkoxy, 1–4C-alkoxycarbonyl, 1–4C-alkylcarbonyl, 1–4C-alkylcarbonyloxy, amino, mono- or di-1–4C-alkylamino or 1–4C-alkylcarbonylamino; $R^{52}$ is hydrogen, hydroxyl, halogen, amino, trifluoromethyl, 1–4C-alkyl or 1–4C-alkoxy, $R^{53}$ is hydrogen, halogen, 1–4C-alkyl or 1–4C-alkoxy; $R^{54}$ hydroxyl, halogen, cyano, carboxyl, 1–4C-alkyl, 1–4C-alkoxy, 1–4C-alkoxycarbonyl or amino; $R^{55}$ is hydrogen, halogen, amino or 1–4C-alkyl; $R^{56}$ is hydrogen or halogen; and $R^{57}$ is hydrogen or halogen; n is 1 or 2; m is 1 or 2; where the sum of m and n may only assume the values 2 or 3, a salt of these compounds and the N-oxide of the pyridines or a salt thereof.

Compounds disclosed in U.S. Pat. No. 6,316,472 (Merck Frosst Canada):

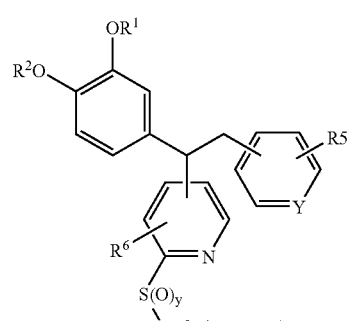

or a pharmaceutically acceptable salt or hydrate thereof wherein:

Y represents N or N-oxide;

y represents 0, 1 or 2;

$R^1$ and $R^2$ are independently selected from H, $C_{1-6}$ alkyl and halo$C_{1-6}$ alkyl;

$R^3$ and $R^4$ are independently selected from H and C.sub.1–6 alkyl, or R.sup.3 and $R^4$ attached to the same carbon atom taken together represent a carbonyl oxygen atom, or $R^3$ and $R^4$ attached to different carbon atoms considered in combination with the carbon atoms to which they are attached along with any intervening atoms and represent a saturated 5, 6- or 7-membered carbocyclic ring;

$R^5$ and R.sup.6 independently represent a member selected from the group consisting of: H, C.sub.1–6 alkyl, haloC.sub.1–6 alkyl and CN;

n represents an integer of from 0–6;

$Ar^1$ is an aromatic group.

Particularly preferred are the following: Rolipram, Arofylline (Almirall), Ariflo® (SmithKline Beecham), Roflumilast (Byk Gulden), Denbufylline (SmithKline Beecham), RS-17597 (Syntex), SDZ-ISQ-844 (Novartis), 4-[2,3-bis(hydroxymethyl)-6,7-diethoxynaphthyl]-1-(2-hydroxyethyl)hydropyridin-2-one (T-440; Tanabe Seiyaku), methyl 3-[6-(2H-3,4,5,6-tetrahydropyran-2-yloxy)-2-(3-thienylcarbonyl)benzo[b]furan-3-yl]propanoate (Bayer), 2-methyl-1-[2-(methylethyl) (8-hydropyrazolo [1,5-a]pyridin-3-yl)]propan-1-one (Ibudilast; Kyorin), N-(3,5-dichloro (4-pyridyl)) (3-cyclopentyloxy-4-methoxyphenyl) carboxamide (RP 73401; Rhône-Poulenc Rorer), (1E)-1-aza-2-(3-cyclopentyloxy-4-methoxyphenyl)prop-1-enyl aminooate (PDA-641; American Home Products), 4-cyano-4-(3-cyclopentyloxy-4-methoxyphenyl)cyclohexanecarboxylic acid (SB207499; SmithKline Beecham), Cipamfylline (SmithKline Beecham), 5-[3-((2S)bicyclo[2.2.1]hept-2-yloxy)-4-methoxyphenyl]-1,3-diazaperhydroin-2-one (CP-80633; Pfizer), 1-(3-nitrophenyl)-3-(3-pyridylmethyl)-1,3-dihydropyridino[2,3-d]pyrimidine-2,4-dione (RS-25344; Syntex), 4-((1R)-1-phenyl-2-(4-pyridyl)ethyl)-2-cyclopentyloxy-1-methoxybenzene (CDP-840; Celltech), (3-{[(3-cyclopentyloxy-4-methoxyphenyl)methyl]amino}pyrazol-4-yl) methan-1-ol, Ro-20-1724 (Roche Holding AG), Piclamilast, Doxofylline (Instituto Biologico Chemioterapico ABC SpA), RPR-132294 (Rhône-Poulenc Rorer), RPR-117658A (Rhône-Poulenc Rorer), L-787258 (Merck Frosst Canada), E-4021 (Eisai Co. Ltd.), GF-248 (Glaxo Wellcome), SKF-107806 (SmithKline Beecham), IPL-4088 (Inflazyme Pharmaceuticals Ltd.), {3-[(3-cyclopentyloxy-4-methoxyphenyl)methyl]-8-(methylethyl)purin-6-yl}ethylamine (V-11294A; Napp Research Centre Ltd.), Atizoram (Pfizer), 5-(3-cyclopentyloxy-4-methoxyphenyl)pyridine-2-carboxamide (CP-353164; Pfizer), methyl 3-[2,4-dioxo-3-benzyl-1,3-dihydropyridino[2,3-d]pyrimidinyl]benzoate (CP-77059; Pfizer), CP-146523 (Pfizer), CP-293321 (Pfizer), CI-1044 (Pfizer), PD-189659(Pfizer), CI-1018 (Pfizer), CP-220629 (Pfizer), 1-(3-nitrophenyl)-3-(4-pyridylmethyl)-1,3-dihydropyridino[2,3-d]pyrimidine-2,4-dione (RS-25344-000; Roche Bioscience), Mesopram (Schering AG), N-(2,5-dichloro(3-pyridyl))(8-methoxy(5-quinolyl))carboxamide (D-4418; Chiroscience), T-2585 (Tanabe Seiyaku), 4-[4-methoxy-3-(5-phenylpentyloxy)phenyl]-2-methylbenzoic acid, XT-044 (Hokuriku University), XT-611 (Kanzawa University), WAY-126120 (Wyeth-Ayerst Pharmaceuticals Inc.), 1-aza-10-(3-cyclopentyloxy-4-methoxyphenyl)-7,8-dimethyl-3-oxaspiro[4.5]dec-7-en-2-one (WAY-122331; Wyeth-Ayerst Pharmaceuticals Inc.), [(3S)-3-(3-cyclopentyloxy-4-methoxyphenyl)-2-methyl-5-oxopyrazolidinyl]-N-(3-pyridylmethyl)carboxamide (WAY-127093B; Wyeth-Ayerst Pharmaceuticals Inc.), PDB-093 (Wyeth-Ayerst Pharmaceuticals Inc.), 3-(1,3-dibxobenzo[c]azolin-2-yl)-3-(3-cyclopentyloxy-4-methoxyphenyl)propanamide (CDC-801; Celgene Corp.), CC-7085 (Celgene Corp.), CDC-998 (Celgene Corp.), NCS-613 (CNRS), CH-3697 (Chiroscience), CH-3442 (Chiroscience), CH-2874 (Chiroscience), CH-4139 (Chiroscience), RPR-114597 (Rhône-Poulenc Rorer), RPR-122818 (Rhône-Poulenc Rorer), (7aS,7R)-7-(3-cyclopentyloxy-4-methoxyphenyl)-7a-methyl-2,5,6,7,7a-pentahydro-2-azapyrrolizin-3-one, GW-3600 (Glaxo-Wellcome), KF-19514 (Kyowa Hakko Kogyo Co Ltd.), CH-422 (Celltech Group), CH-673 (Celltech Group), CH-928 (Celltech Group), D-22888 (Asta Medica), AWD-12-232 (Asta Medica), YM-58997 (Yamanouchi), IC-485 (ICOS Corp.), KW-4490 (Kyowa Hakko Kogyo Co. Ltd.), YM-976 (Yamanouchi), Sch-351591 (Celltech Group), AWD-12-343 (Asta Medica), N-(3,5-dichloro(4-pyridyl))-2-{1-[(4-fluorophenyl)methyl]-5-hydroxyindolin-3-yl}-2-oxoacetamide (AWD-12-281; Asta Medica), Ibudilast (Kyorin Pharmaceutical Co. Ltd.), Cilomilast (SmithKline Beecham), BAY-19-8004 (Bayer), methyl 3-{2-[(4-chlorophenyl)carbonyl]-6-hydroxybenzo[b]furan-3-yl}propanoate, 5-methyl-4-[(4-methylthiophenyl)carbonyl]-4-imidazolin-2-one, 5,6-diethoxybenzo[b]thiophene-2-carboxylic acid (Tibenelast), and 4-(3-bromophenyl)-1-ethyl-7-methylhydropyridino[2,3-b]pyridin-2-one (YM-58897; Yamanouchi).

In one embodiment, the invention provides for the use of a PDE inhibitor, preferably a PDE4 inhibitor, for triggering ovulation after follicular growth and maturation has been induced with FSH. Also within the scope of the invention is the use of a PDE inhibitor, particularly a PDE4 inhibitor, for triggering ovulation after follicular growth and maturation has been induced with a compound or preparation having FSH activity. A particularly preferred substitute for or adjuvant to FSH treatment is an aromatase inhibitor, for example, YM-511 (Yamanouchi), Letrozole (Novartis), Anastrozole (AstraZeneca) or Fadrozole (Novartis). In a preferred regimen for assisted reproductive technologies (ART), in which it is desired to obtain multiple oocytes for in vitro fertilization, patients are administered an aromatase inhibitor (e.g., at or about 2.5–5 mg/day of Letrozole, or Anastrozole) from at or about day 3 to at or about day 7, or from at or about day 3 to at or about day 8 of the menstrual cycle, together with at or about 50–225, preferable 50–150 IU FSH/day, starting on or about day 3 to day 7 of the menstrual cycle, FSH continuing until there are at least two leading follicles having a mean diameter of greater than or equal to at or about 16 mm. At this point, a PDE inhibitor, preferably a PDE4 inhibitor is administered in a dose sufficient to trigger ovulation.

Alternatively, the aromatase inhibitor may be used as the sole follicle growth stimulating agent (i.e., in the absence of FSH), by using a higher dose of aromatase inhibitor (e.g., 2–10 mg/day of Letrozole or Anastrozole) and/or by prolonging administration (e.g., days 3 to 8, 3 to 9, or 3 to 10). When follicular maturation is judged sufficient by sonography, an ovulation triggering dose of PDE inhibitor, preferably PDE4 inhibitor is given. This regimen permits the collection of multiple oocytes, while avoiding injections, as all the agents used are orally available.

In ovulation induction, it is desirable to cause the release of only one ovum. This can be achieved, according to the invention, using FSH to stimulate follicular growth and maturation, followed by administration of a PDE inhibitor, preferably a PDE4 inhibitor, to trigger ovulation. Also within the scope of the invention are ovulation induction regimens in which follicular growth and maturation is induced with a substitute for FSH, for example an aromatase inhibitor.

In a preferred regimen for ovulation induction, a patient is administered a dose of aromatase inhibitor (e.g., 2.5–5 mg/day of Letrozole or Anastrozole) from at or about day 3 to at or about day 7, or from at or about day 5 to at or about day 9 of the menstrual cycle (in the absence of FSH). Alternatively, a single dose of aromatase inhibitor may be given (e.g., 5–30 mg of Letrozole or Anastrozole, preferably 10 or 20 mg), at or about day 3 or day 4 of the menstrual cycle. Ovulation is triggered with an ovulation triggering dose of a PDE inhibitor preferably a PDE4 inhibitor. This regimen provides an ovulation induction protocol that requires no injections.

VI. Pharmaceutical Compositions

The non-polypeptide cAMP level modulators and agents which increase FSH concentrations in a female host (also referred to herein as "active compounds") of the invention, and derivatives, fragments, analogs and homologs thereof, can be incorporated into pharmaceutical compositions suitable for administration. Such compositions typically comprise the active compounds and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of *Remington's Pharmaceutical Sciences*, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, (e.g., intravenous, intradermal, subcutaneous), oral, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The preferred route of administration for non-polypeptide cAMP level modulators including phosphodiesterase inhibitors, as well as for clomiphene, selective estrogen receptor modulators, aromatase inhibitors and inhibitors of steroidogenic enzymes is by oral administration. These active compounds also can be administered subcutaneously by injection, intravenously or trans-vaginally (for local administration). The preferred route of administration of FSH, LH or hCG is by subcutaneous injection, but could also be administered intravenously.

The compounds can also be prepared in the form of suppositories (e.g., with conventional suppository bases such as cocoa butter and other glycerides) or retention enemas for rectal or vaginal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also *Remington's Pharmaceutical Sciences*. In general, a suitable effective dose of one or more compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g., 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage.

The pharmaceutical compositions can be included in a container, pack, or dispenser together with instructions for administration.

The following non-limiting examples are illustrative of the invention.

VII. Exemplification

An in Vivo ovulation model was been developed in which FSH is administered to immature rats bid×2 or 3 days to induce follicular maturation, followed by a single ovulatory dose of hCG. A single injection of non-polypeptide CAMP level modulators (e.g., Compound 1, Compound 2, etc.) co-administered with a sub-ovulatory dose of hCG or injected alone resulted in an induction of ovulation. These results are consistent with a model in which increased CAMP levels enhance or substitute for hCG but not FSH. The role of FSH in any ovulation induction regimen is for promoting follicular development and maturation, not ovulation induction.

The Compounds of Examples 1 through 9 are identified as follows: Compound 1 is Cis-4-cyano-4-(3-(cyclopentyloxy)-4-methoxyphenyl) cyclohexane-1-carboxylic acid; Compound 2 is 3-(Cyclopentyloxy)-N-(3,5-dichloropyridin-4-yl)-4-methoxybenzamide; Compound 3 is 2-(4-(6,7-Diethoxy-2,3-bis (hydroxymethyl) naphthalen-1-yl) pyridin-2-yl)-4-(3-pyridyl) pthalazin-1 (2H)-one hydrochloride; and Compound 4 is 7-Benzylamino-6-chloro-2-piperazino-4-pyrrolidinopteridine.

EXAMPLE 1

Figure 2:
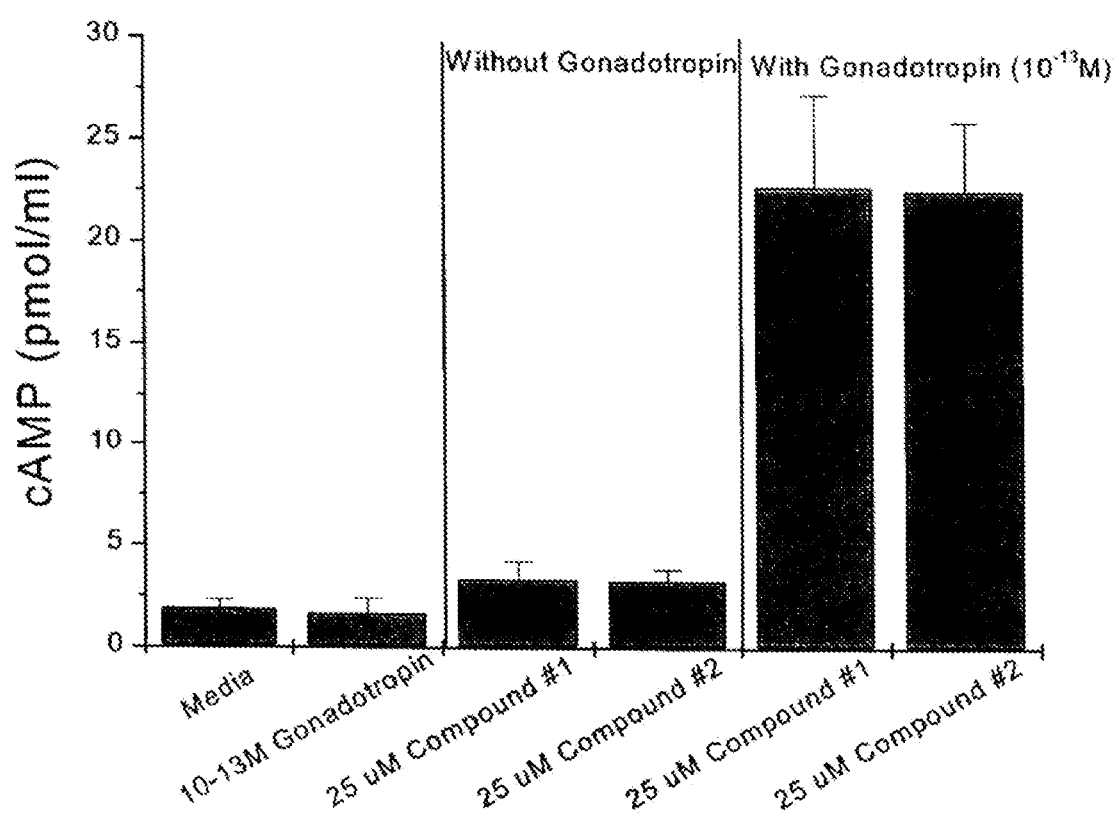
FIG. 2 is a bar graph representation of the effect of phosphodiesterase inhibitors in vitro (i.e., Compound 1 and Compound 2) on increasing intracellular CAMP levels in granulosa cells.

Effect of Compounds 1 and Compounds 2 on Rat Ovarian Granulosa Cell CAMP Levels, Alone or with Gonadotropins In Vitro Ovaries were removed from immature 25 day old, hypophysectomized, diethylstilbesterol treated Sprague-Dawley rats. The ovaries were repeatedly punctured with 27 gauge needles to liberate granulosa cells from the follicles. Cells were washed and re-suspended in McCoys 5A media+0.1% BSA+2 µM androstenedione. Viable cells in number of 100,000 were loaded into 6-well tissue culture dishes in a 1.0 ml volume (with Compound 1 and Compound 2 at a concentration of 25 micromolar, either alone or in conjunction with a low, 0.1 pM dose of gonadotropin). Plates were incubated in a 37° C. incubator, 100% humidity, 5.0% $CO_2$ for 48 hrs. Conditioned media were assayed in a CAMP specific RIA. Results are expressed as mean plus or minus standard deviations. As seen in FIG. 2, Compounds 1 and 2 cause a significant increase in CAMP levels in the presence of sub-effective concentrations of gonadotropin.

EXAMPLE 2

Effect of the PDE Inhibitor Compound 1 on Follicle Maturation In Vivo

Mature ovarian follicles generated in immature female rats by treatment with a sub-optimal dose of FSH (1.08 IU/rat/injection; bid×3 days) with and without co-administration of Compound 1 (0.1, 1, 10, and 50 mg/kg/injection: bid×3 days). A single injection of an ovulatory dose of hCG (20 IU) was administered with the final FSH injection. The PDE inhibitors were given in conjunction with sub-optimal doses of FSH.

Figure 3:
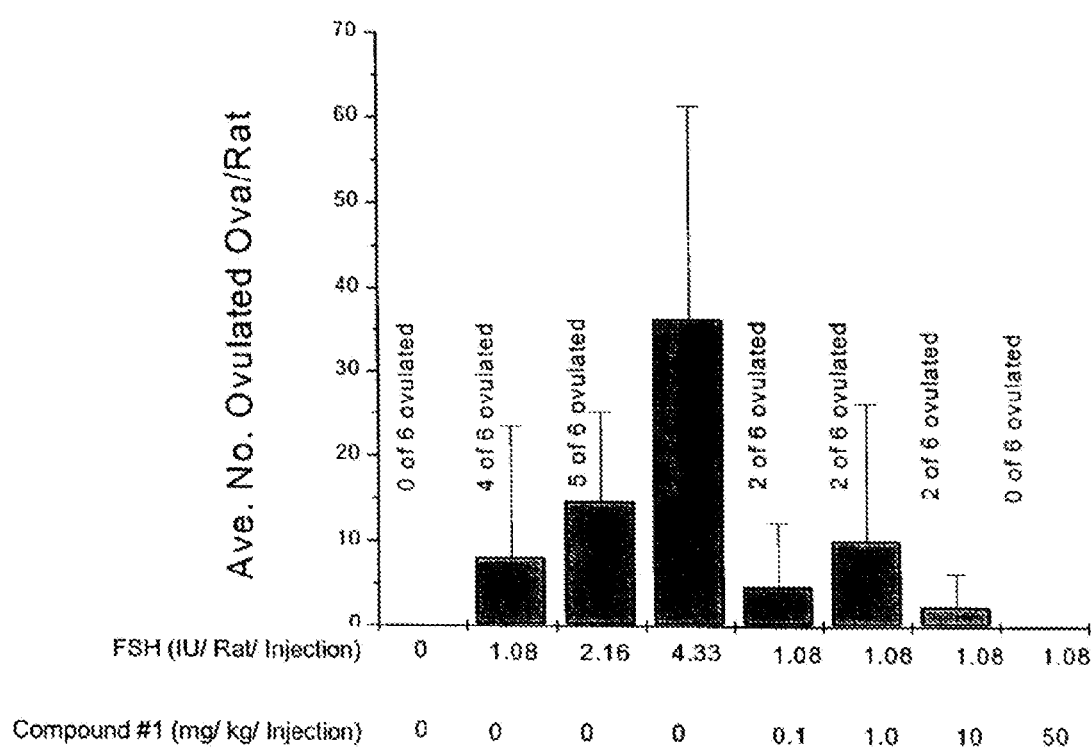
FIG. 3 is a bar graph representation of the effect of a phosphodiesterase inhibitor (i.e., Compound 1) on follicle maturation in rats, in vivo.

All injections were subcutaneously administered. Ovulation was determined 18 hours after hCG administration by counting oocytes in oviduct. Results are expressed as mean plus or minus standard deviations. As seen in FIG. 3, data represent average number of oocytes in oviducts of all rats in each group and frequency of ovulating rats. As also noted in FIG. 3, a PDE inhibitor (Compound 1) inhibited (rather than stimulated) both ovulation administered at 50 mg/kg. The results demonstrate that increasing doses of PDE inhibitor failed to enhance the ability of a sub-optimal dose of FSH to prepare follicles to ovulate.

EXAMPLE 3

Figure 4:
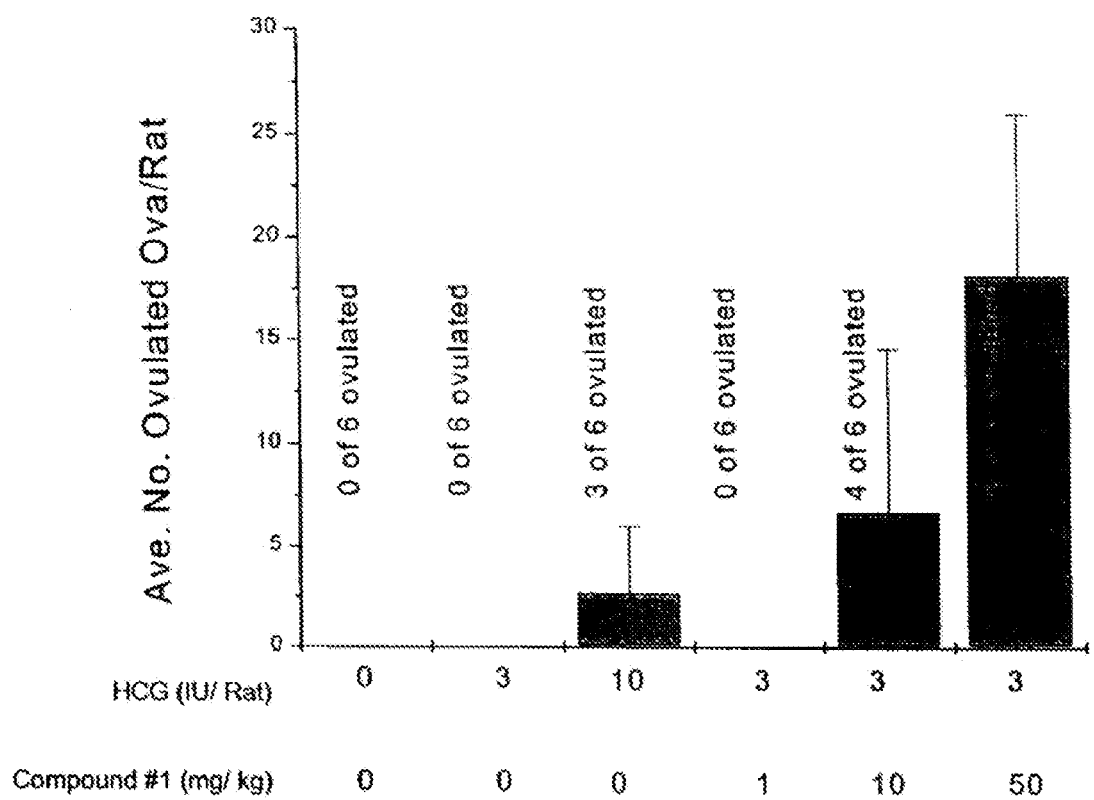
FIG. 4 is a bar graph representation of the effect of a phosphodiesterase inhibitor (i.e., Compound 1) on ovulation with CG in rats, in vivo.

Effect of the PDE Inhibitor Compound 1 on Ovulation, in the Presence of a Sub-Effective Dose of hCG In Vivo Mature ovarian follicles generated in immature female rats by treatment with an effective dose of FSH (2.16 IU/rat/injection; bid×2 days) were induced to ovulate with a single injection of hCG. hCG was administered at a sub-effective dose (3 IU) with and without a single injection of Compound 1 (50, 10 and 1 mg/kg) at the time of the final FSH injection. Ovulation was determined 18 hours after hCG administration by counting the number of ova in the oviduct. As seen in FIG. 4, a single injection of Compound 1 co-administered with a sub-ovulatory dose of hCG resulted in an induction of ovulation. All injections were subcutaneous. Results are expressed as mean plus or minus standard deviations. This data demonstrates that a non-polypeptide CAMP level modulator, in this case a PDE inhibitor enhances hCG-stimulated ovulation when a sub-optimal dose of hCG is administered. The effects of Compound 1, a known PDE inhibitor, are shown.

EXAMPLE 4

Figure 5:
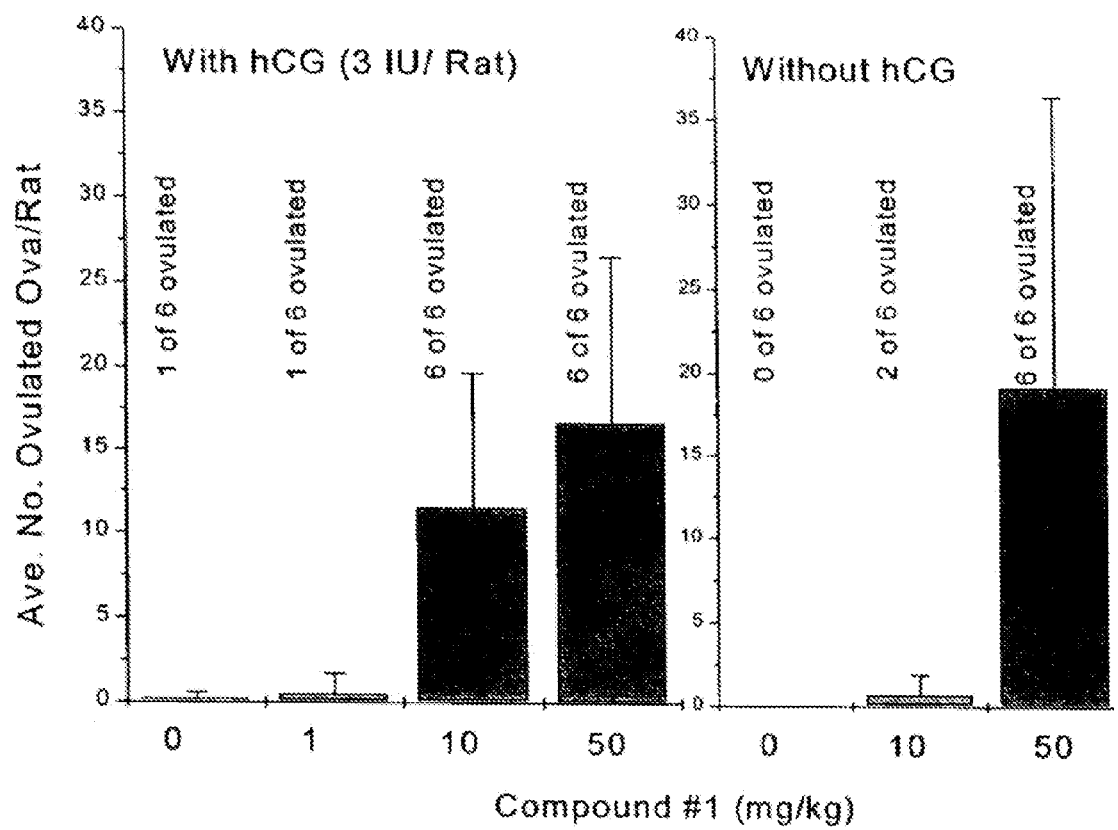
FIG. 5 is a bar graph representation of the effect of a phosphodiesterase inhibitor (i.e., Compound 1) on ovulation with and without CG in rats, in vivo.

Effect of PDE Inhibitor Compound 1 on Ovulation in the Presence or Absence of a Sub-Effective Dose of hCG In Vivo Following FSH induced follicular maturation (2.16 IU/rat/injection; bid×2 days) Compound 1 was injected with and without a sub-effective dose of hCG. Ovulation was determined 18 hours after hCG/Compound 1 administration by counting oocytes in oviduct. Data represent average number of oocytes in oviducts of all rats in each group and frequency of ovulating rats. As seen in FIG. 5, a single injection of Compound 1 administered alone, without a sub-ovulatory dose of hCG, resulted in an induction of ovulation in FSH pretreated rats. Results are expressed as mean plus or minus standard deviations. This data demonstrates that a non-polypeptide CAMP level modulator, in this case a PDE inhibitor, Compound 1, is able to induce ovulation in the absence of any injected hCG. Previous experiments, and those presented here have shown that follicles prepared with these doses of FSH do not ovulate spontaneously, but require subsequent hCG administration.

EXAMPLE 5

Figure 6:
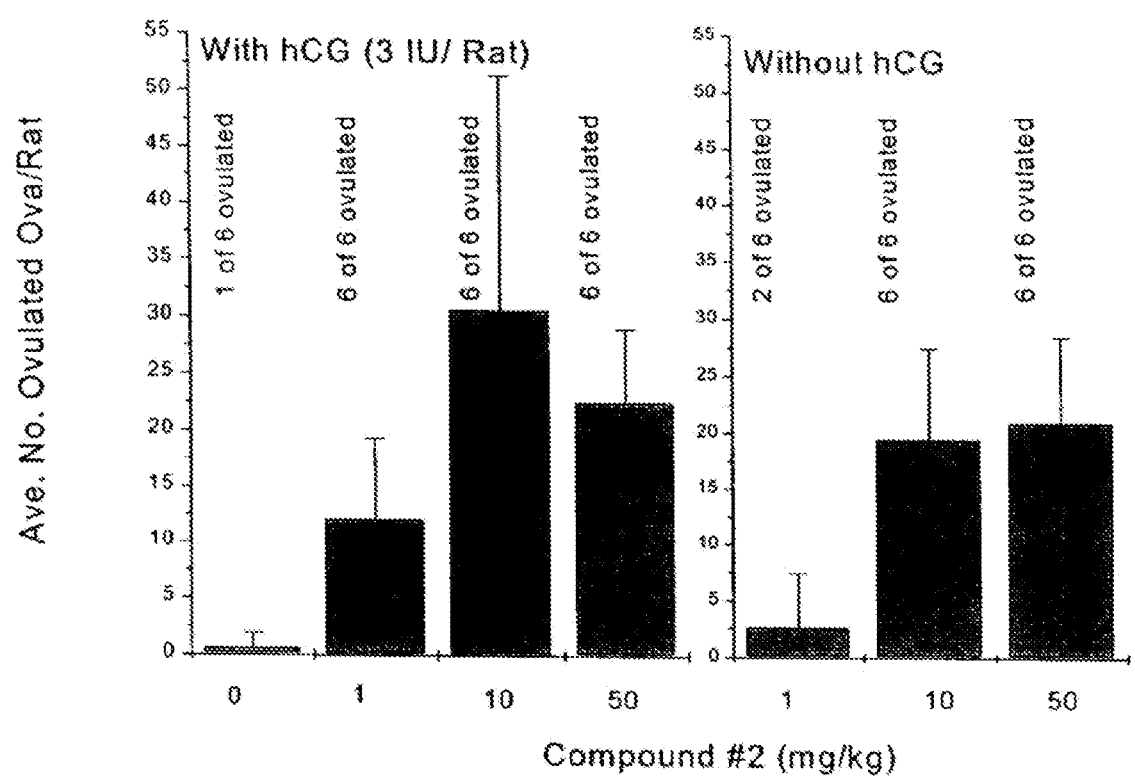
FIG. 6 is a bar graph representation of the effect of a phosphodiesterase inhibitor (i.e., Compound 2) on ovulation with and without CG in rats, in vivo.

Effect of PDE inhibitor Compound 2 on Ovulation in the Presence or Absence of a Sub-Effective Dose of hCG In Vivo Following FSH induced follicular maturation (2.16 IU/rat/injection; bid×2 days) Compound 2 was injected with and without a sub-effective dose of hCG. Ovulation was determined 18 hours after hCG/Compound 2 administration by counting oocytes in oviduct. Data represent average number of oocytes in oviducts of all rats in each group and frequency of ovulating rats. Results are expressed as mean plus or minus standard deviations. As seen in FIG. 6, a single injection of Compound 2 administered alone, without a sub-ovulatory dose of hCG, resulted in an induction of ovulation in FSH pretreated rats. This data demonstrates that a non-polypeptide CAMP level modulator, in this case a PDE inhibitor, Compound 2, is able to induce ovulation in the absence of any injected hCG.

EXAMPLE 6

Figure 7:
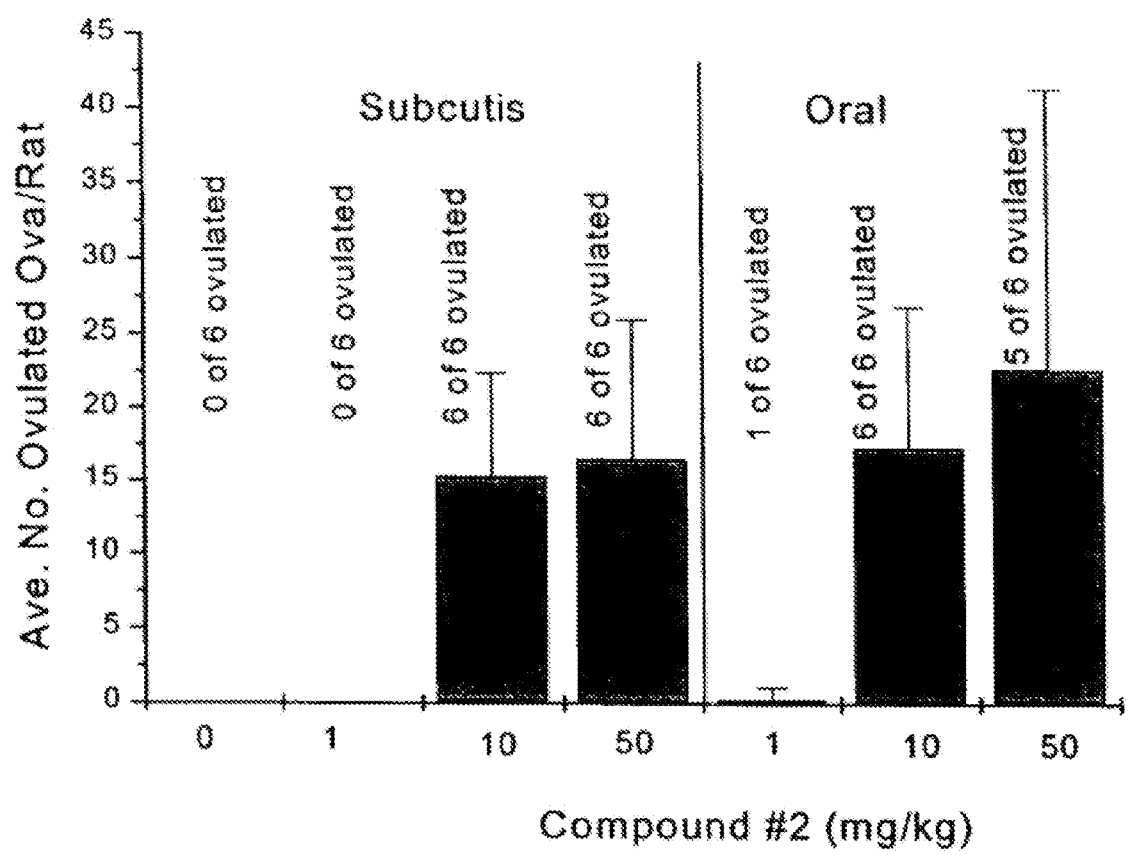
FIG. 7 is a bar graph representation of the effect of a phosphodiesterase inhibitor (i.e., Compound 2) on ovulation following oral and subcutaneous administration.

Effect of PDE Inhibitor Compound 2 on Ovulation In Vivo Following Oral and Subcutaneous Administration Following FSH induced follicular maturation (2.16 TU/rat/injection; bid×2 days) Compound 2 was either injected subcutaneously (subcutis) or administered by oral gavage. Ovulation was determined 18 hours after Compound 2 administration by counting oocytes in oviduct. Data represent average number of oocytes in oviducts of all rats in each group and frequency of ovulating rats. Results are expressed as mean plus or minus standard deviations. A s seen in FIG. 7, administration of Compound 2 by either subcutaneous or oral route resulted in an induction of ovulation in FSH pretreated rats. This data demonstrates that a non-polypeptide CAMP level modulator, in this case a PDE inhibitor, Compound 2, is able to induce ovulation when administered orally.

EXAMPLE 7

Figure 8:
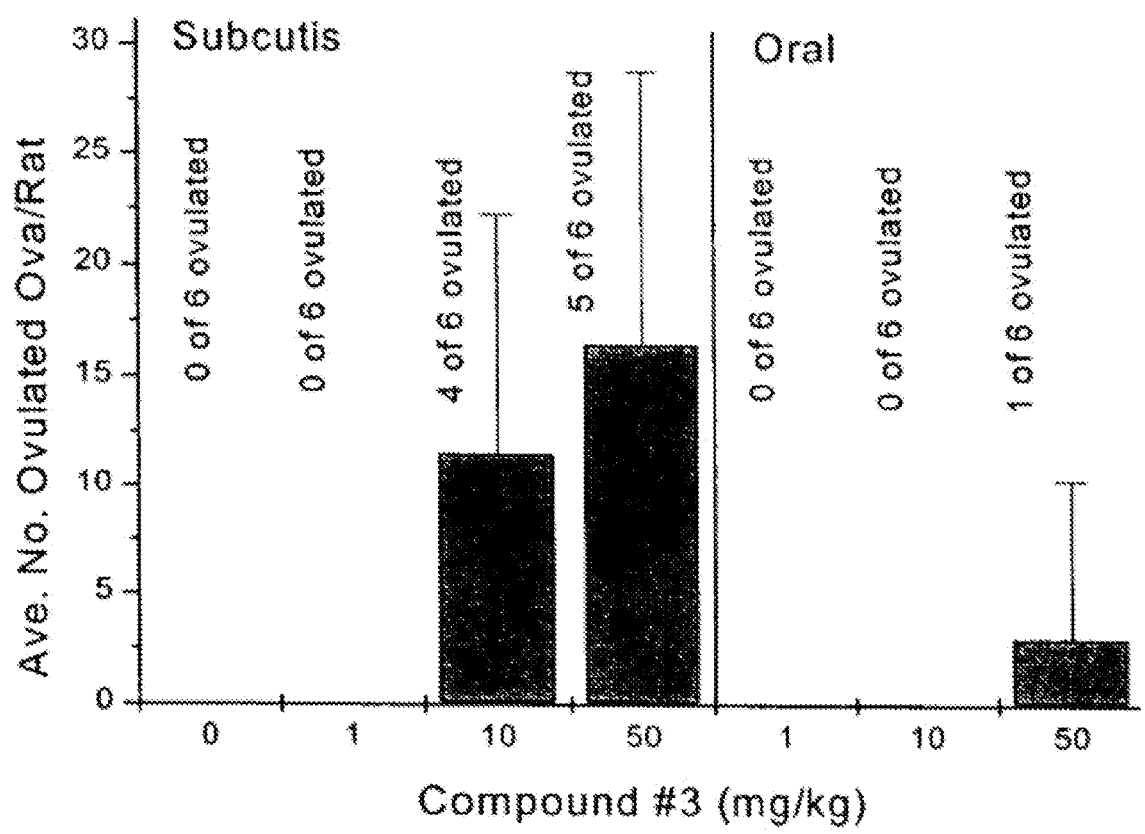
FIG. 8 is a bar graph representation of the effect of PDE inhibitor Compound 3 on ovulation in vivo following oral and subcutaneous administration.

Effect of PDE Inhibitor Compound 3 on Ovulation In Vivo Following Oral and Subcutaneous Administration Following FSH induced follicular maturation (2.16 IU/rat/injection; bid×2 days) Compound 3 was either injected subcutaneously (subcutis) or administered by oral gavage. Ovulation was determined 18 hours after Compound 2 administration by counting oocytes in oviduct. Data represent average number of oocytes in oviducts of all rats in each group and frequency of ovulating rats. Results are expressed as mean plus or minus standard deviations. As seen in FIG. 8, administration of Compound 3 by either subcutaneous or oral route resulted in an induction of ovulation in FSH pretreated rats. This data demonstrates that a non-polypeptide cAMP level modulator, in this case a PDE inhibitor, Compound 3, is able to induce ovulation when administered orally.

EXAMPLE 8

Figure 9:
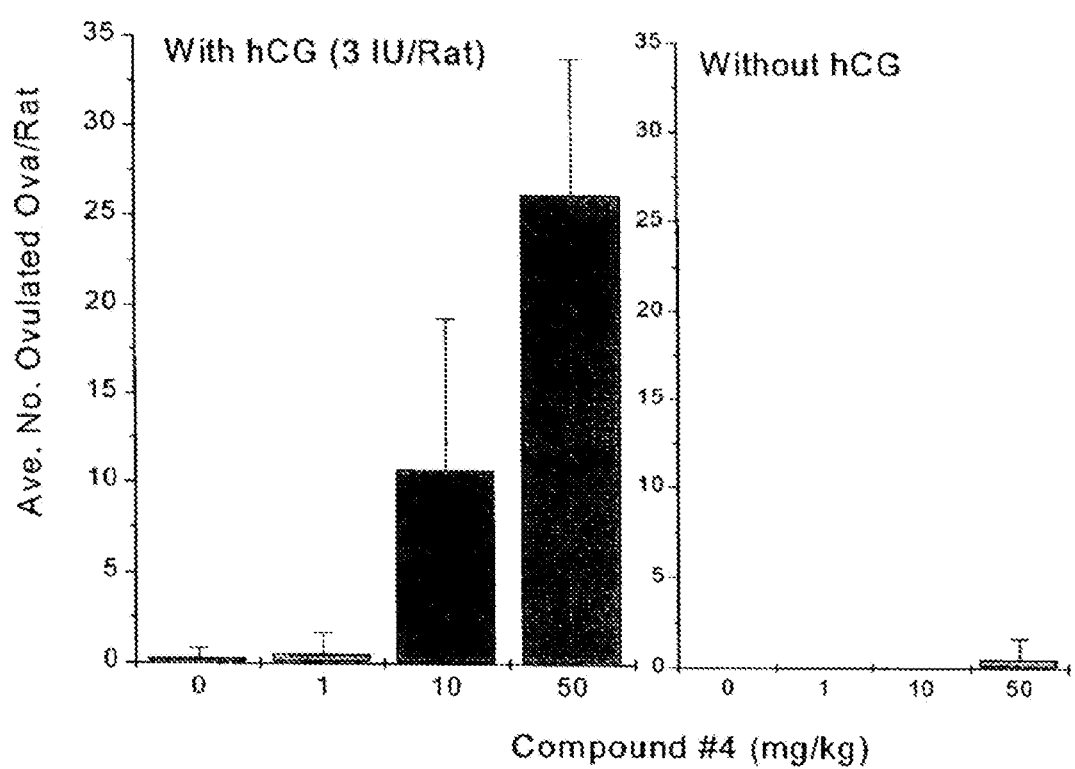
FIG. 9 is a bar graph representation of the effect of PDE inhibitor Compound 4 on ovulation in the presence or absence of a sub-effective dose of hCG in vivo.

Effect of PDE Inhibitor Compound 4 on Ovulation in the Presence or Absence of a Sub-Effective Dose of hCG In Vivo Following FSH induced follicular maturation (2.16 IU/rat/injection; bid×2 days) Compound 4 was injected subcutaneously with and without a sub-effective dose of hCG. Ovulation was determined 18 hours after hCG/Compound 4 administration by counting oocytes in oviduct. Data represent average number of oocytes in oviducts of all rats in each group and frequency of ovulating rats. As seen in FIG. 9, a single injection of Compound 4 administered with a sub-ovulatory dose of hCG resulted in an induction of ovulation in FSH pretreated rats. Compound 4 administered alone induced little or no ovulation. Results are expressed as mean plus or minus standard deviations. This data demonstrates that a non-polypeptide cAMP level modulator, in this case a PDE inhibitor, Compound 4, which is insufficient to induce ovulation alone, is able to induce ovulation in the presence of a sub-effective dose of hCG.

EXAMPLE 9

Effect of PDE Inhibitor Compound 2 on Ovulation and Fertility

Figure 10:
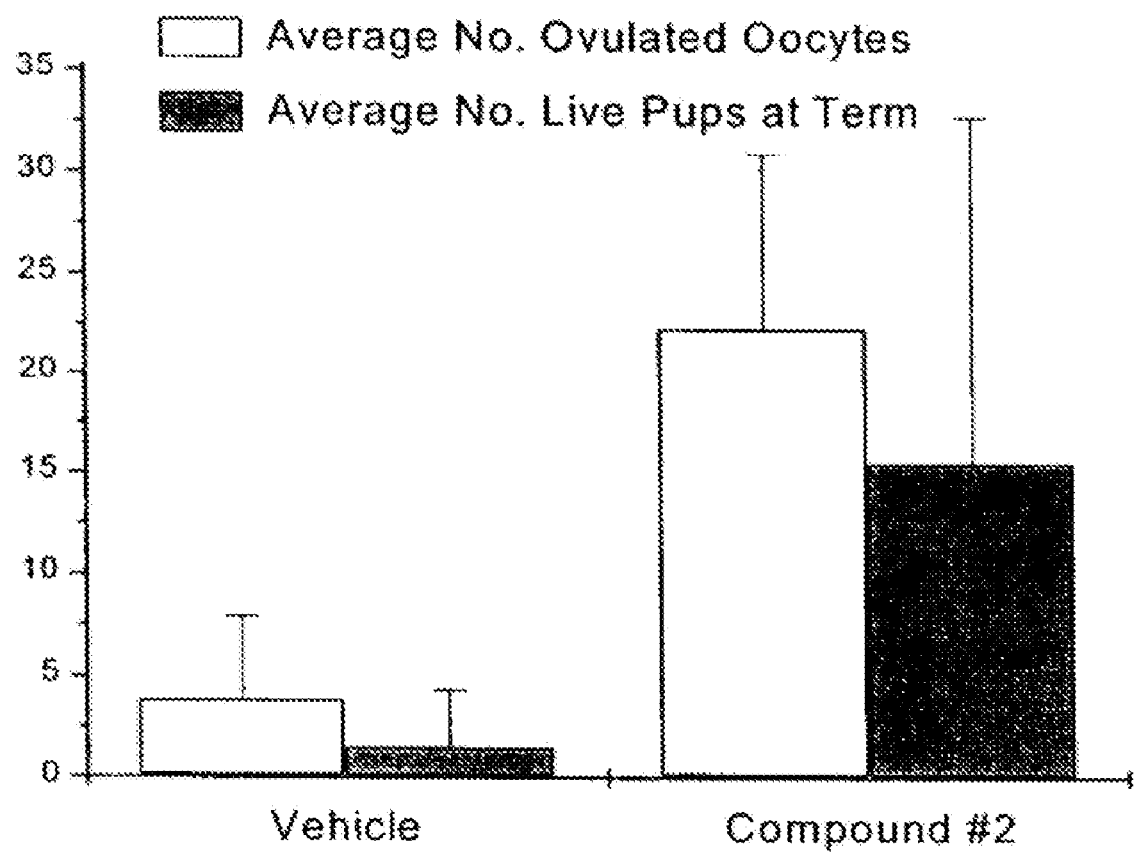
FIG. 10 is a bar graph representation of the effect of PDE inhibitor Compound 2 on ovulation and fertility.

Follicular maturation was induced in immature rats with FSH (4.33 IU/rat/injection; bid×2 days) and Pregnant Mare's Serum Gonadotropin (PMSG) (1.5 IU/rat/injection; bid×2 days). This combination was previously found to induce follicular maturation and promote mating behavior while maintaining a low spontaneous ovulation rate in the absence of an additional injection of hCG. FSH and PMSG induced rats were then treated with either Compound 2 (12 rats) or vehicle (12 rats) by subcutaneous administration. In one cohort of rats (6 rats per treatment), ovulation was determined 18 hours after Compound 2 or vehicle administration by counting oocytes in oviduct. To assess fertility, another cohort of rats (6 rats per treatment) were individually placed overnight in a cage together with a single adult male rat of proven fertility. The next day, male rats were removed and the females were caged together by group until the day of parturition. The number of live full-term pups observed at the time of parturition was recorded. As seen in FIG. 10, a single injection of Compound 2 resulted in an induction of ovulation in FSH/PMSG pretreated rats. In addition, rats treated with Compound #2 had an increased number of live pups at the time of parturition. Results for both ovulation and live pups are expressed as mean plus or minus standard deviations. This data demonstrates that a non-polypeptide CAMP level modulator, in this case a PDE inhibitor, Compound 2, induces ovulation of oocytes which are capable of being fertilized in vivo.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The entire contents of all references, patents and published patent applications cited throughout this application are hereby incorporated by reference.

Adashi et al (Eds.) *Reproductive Endocrinology, Surgery, and Technology*, Volumes 1 and 2, Lippincott-Raven Publishers, Philadelphia (1996)

Bär T, "Benzamides with Tetrahydrofuranyloxy Substituents as Phosphodiesterase 4 Inhibitors", U.S. Pat. No. 6,303,789, issued Oct. 16, 2001

Bräunlich et al, "3-Ureido-Pyridofurans and Pyridothiophenes for the Treatment of Inflammatory Processes", international publication WO 98/02440 of Jan. 22, 1998

Chappel S, "Novel Method of Ovulation Induction in Humans", U.S. Pat. No. 5,087,615, issued Feb. 11, 1992

Cooke G M, "Differential effects of trilostane and cyanoketone on the 3 beta-hydroxysteroid dehydrogenase-isomerase reactions in androgen and 16-androstene biosynthetic pathways in the pig testis", *J Steroid Biochem Mol Biol* 58:1 95–101 (1996)

Frenette et al, "Heterosubstituted Pyridine Derivatives as PDE 4 Inhibitors", U.S. Pat. No. 6,316,472, issued Nov. 13, 2001

Freyne et al, "PDE IV Inhibiting 2-Cyanoiminoimidazole Derivatives", international publication WO 98/14432 of Apr. 9, 1998

Guay et al, "Diphenyl Pyridyl Ethane Derivatives as PDE IV Inhibitors", U.S. Pat. No. 5,710,160, issued Jan. 20, 1998

Guay et al, "Tri-aryl Ethane Derivatives as PDE IV Inhibitors", U.S. Pat. No. 5,710,170, issued Jan. 20, 1998

Hersperger R, "Naphthyridine Derivatives", international publication WO 98/18796 of May 6, 1998

Cox et al, "Substituted Azabicyclic Compounds and Their Use as Inhibitors of the Production of TNF and Cyclic AMP Phosphodiesterase", international publication WO 97/48697 of Dec. 24, 1997

Dyke et al, "Quinoline Carboxamides as TNF Inhibitors and as PDE-IV Inhibitors", international publication WO 97/44036 of Nov. 27, 1997

Dyke et al, "Quinoline Sulfonamides as TNF Inhibitors and as PDE-IV Inhibitors", international publication WO 97/44322 of Nov. 27, 1997

Dyke et al, "Benzofuran Carboxamides and Their Therapeutic Use", international publication WO 97/44337 of Nov. 27, 1997

Dyke et al, "Quinolines and Their Therapeutic Use", international publication WO 98/20007 of May 14, 1998

Marfat, A., "Substituted Indazole Derivatives and Their Use as Inhibitors Phosphodiesterase (PDE) Type IV and the Production of Tumor Necrosis Factor (TNF), international publication WO 97/42174 of Nov. 13, 1997

Marfat A, "Substituted Indazole Derivatives and Their Uses as Phosphodiesterase (PDB) Type IV and Tumor Necrosis Factor (TNF) Inhibitors", international publication WO 97/49702 of Dec. 31, 1997

Shetty et al, "Effect of estrogen deprivation on the reproductive physiology of male and female primates", *J Steroid Biochem Mol Biol* 61:(3–6):157–166 (1997)

Shoham et al (Eds.) *Female Infertility Therapy Current Practice*; Martin Dunitz Ltd, London (1999)

Shughrue et al, "Regulation of progesterone receptor messenger ribonucleic acid in the rat medial preoptic nucleus by estrogenic and antiestrogenic compounds: an in situ hybridization study", *Endocrinology*, 1999 138(12):5476–5484 (1999)

Turner et al, "Effect of chronic administration of an aromatase inhibitor to adult male rats on pituitary and testicular function and fertility", *J Endocrinol* 164(2):225–238 (2000)

What is claimed is:

1. A method of combined treatment for stimulating follicular development and ovulation induction in a female host comprising:

(a) administering an agent which increases follicle stimulating hormone concentrations in the host during the follicular phase of the host's ovulatory cycle; and
(b) administering an inhibitor of a phosphodiesterase 4 isoform to the host prior to the luteal phase of the host's ovulatory cycle.

2. The method of claim 1, wherein the agent is follicle stimulating hormone.

3. The method of claim 1 wherein luteinizing hormone is also administered to the host to induce ovulation prior to the luteal phase of the host's ovulatory cycle.

4. The method of claim 3, wherein the inhibitor of a phosphodiesterase 4 isoform and luteinizing hormone are coadministered.

5. The method of claim 4, wherein the coadministration is sequential.

6. The method of claim 4, wherein the coadministration is simultaneous.

7. The method of claim 4, wherein the inhibitor of a phosphodiesterase 4 isoform and luteinizing hormone are administered by the same mode of delivery.

8. The method of claim 4, wherein the inhibitor of a phosphodiesterase 4 isoform and luteinizing hormone are administered by different modes of delivery.

9. The method of claim 1, wherein luteinizing hormone is also administered at a dose lower than the amount of luteinizing hormone to induce ovulation in the same host in existing regimens prior to the luteal phase of the host's ovulatory cycle.

10. The method of claim 1, wherein chorionic gonadotropin is also administered to the host to induce ovulation prior to the luteal phase of the host's ovulatory cycle.

11. The method of claim 10, wherein the inhibitor of a phosphodiesterase 4 isoform and chorionic gonadotropin are coadministered.

12. The method of claim 11, wherein the coadministration is sequential.

13. The method of claim 11, wherein the coadministration is simultaneous.

14. The method of claim 11, wherein the inhibitor of a phosphodiesterase 4 isoform and luteinizing hormone are administered by the same mode of delivery.

15. The method of claim 11, wherein the inhibitor of a phosphodiesterase 4 isoform and luteinizing hormone are administered by different modes of delivery.

16. The method of claim 1, wherein chorionic gonadotropin is also administered at reduced a dose lower than the amount of chorionic gonadotropin to induce ovulation in the same host in existing regimens prior to the luteal phase of the host's ovulatory cycle.

17. The method of claim 1 wherein the inhibitor of a phosphodiesterase 4 isoform is administered orally.

* * * * *